(12) United States Patent
Sakamoto et al.

(10) Patent No.: US 7,084,222 B2
(45) Date of Patent: Aug. 1, 2006

(54) RUTHENIUM COMPLEXES, PROCESS FOR PREPARATION THEREOF, AND PROCESSES FOR PRODUCING OPEN-RING POLYMER OF CYCLOOLEFINS AND HYDROGENATION PRODUCTS THEREOF BY USING THE COMPLEX AS CATALYST

(75) Inventors: Masato Sakamoto, Tokyo (JP); Seiji Okada, Tokyo (JP); Yasuo Tsunogae, Tokyo (JP); Shintaro Ikeda, Tokyo (JP); Wolfgang A. Herrmann, Freising (DE); Karl Oefele, Puchheim (DE)

(73) Assignee: Zeon Corporation, Tokyo (JP)

( * ) Notice: Subject to any disclaimer, the term of this patent is extended or adjusted under 35 U.S.C. 154(b) by 0 days.

(21) Appl. No.: 10/489,921

(22) PCT Filed: Sep. 19, 2002

(86) PCT No.: PCT/JP02/09617

§ 371 (c)(1),
(2), (4) Date: Sep. 14, 2004

(87) PCT Pub. No.: WO03/027079

PCT Pub. Date: Apr. 3, 2003

(65) Prior Publication Data

US 2005/0014916 A1    Jan. 20, 2005

(30) Foreign Application Priority Data

Sep. 20, 2001  (JP) .............................. 2001-286219
Sep. 20, 2001  (JP) .............................. 2001-286223

(51) Int. Cl.
*C08F 4/80*   (2006.01)
*C07F 15/00*  (2006.01)

(52) U.S. Cl. ................... 526/171; 526/283; 525/332.1; 525/338; 585/277; 546/4; 556/136

(58) Field of Classification Search ................ 556/136; 526/171, 283; 525/332.1, 338; 546/4; 585/277
See application file for complete search history.

(56) References Cited

U.S. PATENT DOCUMENTS 6,077,805 A  *  6/2000  Van Der Schaaf et al. . 502/155
6,511,756 B1 *  1/2003  Obuchi et al. .............. 428/517
6,552,139 B1 *  4/2003  Herrmann et al. .......... 526/171

FOREIGN PATENT DOCUMENTS

| EP | 0 218 138 A1 | | 4/1987 |
|---|---|---|---|
| JP | 10-195182 A | | 7/1998 |
| JP | 11-335446 A | | 12/1999 |
| JP | 2000-26580 A | | 1/2000 |
| WO | 96/04289 A1 | | 2/1996 |
| WO | 99/20676 | * | 4/1999 |
| WO | 99/51344 A1 | | 10/1999 |
| WO | WO 99/51344 A | | 10/1999 |
| WO | 00/15339 A1 | | 3/2000 |

OTHER PUBLICATIONS

Junji Kodemura et al.; Polymer Journal, vol. 27, No. 12, pp. 1167-1172, 1995.
Richard R. Schrock; Metathesis Polymerization of olefins and Polymerization of Olefins and Polymerization of Alkynes, 1996, p. 1, Kluwer Academic Publisher, Boston.

* cited by examiner

*Primary Examiner*—Fred Teskin
(74) *Attorney, Agent, or Firm*—Birch, Stewart, Kolasch & Birch, LLP

(57) ABSTRACT

The present invention relates to ruthenium complex compound wherein a heteroatom-containing carbene compound having a six-membered ring structure is bonded to ruthenium and a process for the preparation thereof; a process for producing ring-opened cyclic olefin polymer by subjecting a cyclic olefin to ring-opening metathesis polymerization in the presence of such a ruthenium complex compound; and a process for producing hydrogenated product of ring-opened cyclic olefin polymers by hydrogenating the carbon-carbon double bonds of the above ring-opened polymers. The invention gives hydrogenated product of ring-opened cyclic olefin polymers having physical properties different from those of hydrogenated product of ring-opened polymers of the prior art. Particularly, the use of dicyclopentadiene can give a hydrogenated product of ring-opened cyclic olefin polymer excellent in heat resistance, and this product can be advantageously used as parts or formed products for medical appliances or electrical components.

11 Claims, 1 Drawing Sheet

RUTHENIUM COMPLEXES, PROCESS FOR PREPARATION THEREOF, AND PROCESSES FOR PRODUCING OPEN-RING POLYMER OF CYCLOOLEFINS AND HYDROGENATION PRODUCTS THEREOF BY USING THE COMPLEX AS CATALYST

TECHNICAL FIELD

The present invention relates to a novel ruthenium complex compound and a process for producing the same, and to a process for producing a ring-opened cyclic olefin polymer and a hydrogenated product of the same using the ruthenium complex compound as a catalyst.

BACKGROUND ART

Metathesis reaction such as ring-opening metathesis polymerization or ring-closing metathesis reaction of an olefin compound, cross metathesis reaction of an acyclic olefin, or metathesis polymerization of an acyclic diene is an industrially advantageous reaction. The metathesis reaction is carried out in the presence of a catalyst. As the catalyst used, a catalyst system comprising a transition metal compound such as tungsten, molybdenum, or titanium and an organometal reducing agent such as an organoaluminum compound or organotin compound in combination has been conventionally known. However, in the catalyst system, a plurality of catalytically active species is produced, and the produced catalytically active species are unstable and soon become deactivated. Therefore, it is difficult to control the metathesis reaction.

In recent years, it has been reported that a transition metal-carbene complex with a carbene compound being bonded to a transition metal exhibits high catalytic activity and can control various metathesis reactions at a high degree. For example, publication of European Patent application No. 218138 and "Metathesis Polymerization of Olefins and Polymerization of Alkynes", 1996, p. 1, Kluwer Academic Publisher, Boston describe that a carbene complex of molybdenum or tungsten having bulky alkoxide and imide ligands is a highly active metathesis reaction catalyst and that a cyclic olefin polymer having comparatively high stereospecificity can be obtained by ring-opening metathesis polymerization of cyclic oleifn when this complex is used.

Nowadays, a ruthenium complex compound with a carbene compound being bonded to ruthenium (hereinafter may be referred to as "ruthenium-carbene complex") which is hardly affected by water or an alcohol has attracted attention. For example, as a highly active metathesis reaction catalyst for an olefin compound, WO 96/04289 describes a ruthenium-carbene complex having a phosphine as a ligand. Japanese Patent Application Laid-open No. 10-195182 describes a process which comprises polymerizing a cyclic olefin by ring-opening metathesis polymerization in the presence of a ruthenium-carbene complex compound having a phosphine as a ligand, followed by hydrogenating olefinic double bonds in the ring-opened polymer without addition of a hydrogenation catalyst.

WO 99/51344 and WO 00/15339 describe a ruthenium-carbene complex having a substituted imidazolin-2-ylidene or substituted imidazolidin-2-ylidene, which is a heterocyclic carbene compound comprising a five-membered ring structure, as a ligand instead of a phosphine. The specifications relate that this catalyst exhibits extremely high catalytic activity and present an example of the reaction using a ruthenium-carbene complex having substituted imidazolin-2-ylidenes with different substituents at the 1-position and 3-position as a ligand. However, since ruthenium is a rare and expensive metal, further activation of a ruthenium-carbene complex has been demanded.

A ring-opened polymer of a cyclic olefin, in particular, a polymer of norbornene monomers and a hydrogenated product of the polymer are amorphous polymers. Therefore, the polymers have been conventionally known to have excellent transparency, heat resistance, low birefringence, formability, and the like, and are suitable as a material for optical disks and optical lenses. Further, the ring-opened polymer and the hydrogenated product have been applied to products other than optical goods, due to their other excellent properties such as low dielecticity and chemical resistance. In particular, a hydrogenated product of a ring-opened polymer of dicyclopentadiene (DCP) which is the most common norbornene monomer exhibits excellent mechanical strength and has been expected to be widely applied to products other than optical goods.

However, the hydrogenated product of ring-opened DCP polymer has a glass transition temperature (Tg) of 97° C. or less (Polymer Journal, 1995, vol. 27, p. 1167) and there is a problem about heat resistance of the product. For example, such a product cannot be used for medical appliances requiring steam sterilization resistance or electric components of which the inside is heated to a high temperature. The polymer must have a Tg of 100° C. or more for such medical appliances and electric components.

Specifically, a hydrogenated product of ring-opened DCP polymer having a Tg of 100° C. or more cannot be obtained, not only in the case of using a conventional catalyst system comprising a transition metal compound and an organometal reducing agent in combination, but also in the case of using a recently proposed molybdenum-carbene complex compound, tungsten-carbene complex compound, or ruthenium-carbene complex compound.

The present invention has been achieved in view of such a situation. An object of the present invention is to provide a novel and highly catalytically active ruthenium complex compound and a process for producing the same, a process for producing a ring-opened cyclic olefin polymer and a hydrogenated product of the same using the ruthenium complex compound as a metathesis reaction catalyst or a hydrogenation catalyst, and a hydrogenated product of ring-opened dicyclopentadiene polymer exhibiting excellent heat resistance.

DISCLOSURE OF THE INVENTION

The present inventors have been successful for the first time in obtaining a ruthenium complex compound with a hetero atom-containing carbene compound having a six-membered ring structure being bonded to ruthenium. The inventors have also found that the ruthenium complex compound is a catalyst highly active to metathesis reaction and hydrogenation of an olefin compound. The inventors have further found that a hydrogenated product obtained by polymerizing a cyclic olefin such as dicyclopentadiene by ring-opened polymerization using the ruthenium complex compound as a metathesis reaction catalyst, followed by hydrogenating carbon-carbon double bonds in the obtained polymer, exhibits high heat resistance. These findings have led to the completion of the present invention.

First, the present invention provides a ruthenium complex compound comprising a hetero atom-containing carbene compound having a six-membered ring structure bonded to ruthenium.

The ruthenium complex compound of the present invention is preferably a compound of the formula [2]:

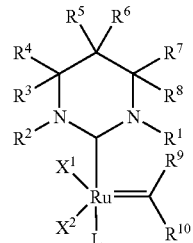

wherein $R^1$–$R^8$ independently represent a hydrogen atom, a halogen atom, or a hydrocarbon group, and at least two of $R^1$–$R^8$ may be bonded together to form a ring, $X^1$ and $X^2$ independently represent an anionic ligand, L represents a neutral ligand, and $R^9$ and $R^{10}$ independently represent a hydrogen atom or an organic group.

The ruthenium complex compound of the present invention is still more preferably a compound of the formula [2], wherein $R^1$ and $R^2$ are independently an alkyl group having 1–20 carbon atoms or an aryl group having 6–20 carbon atoms, and either $R^9$ or $R^{10}$ is a hydrogen atom and the other is an alkoxyl group having 1–20 carbon atoms or an aryl group having 6–20 carbon atoms.

Second, the present invention provides a process for producing the ruthenium complex compound, comprising reacting a hetero atom-containing carbene compound having a six-membered ring structure with a ruthenium complex compound having a neutral ligand.

Third, the present invention provides a metathesis reaction catalyst for an olefin compound, comprising the ruthenium complex compound of the present invention. The metathesis reaction catalyst of the present invention can be suitably used as a ring-opening metathesis polymerization catalyst.

Fourth, the present invention provides a hydrogenation catalyst for an olefin compound, comprising the ruthenium complex compound of the present invention.

Fifth, the present invention provides a process for producing a ring-opened cyclic olefin polymer, comprising polymerizing a cyclic olefin by ring-opening metathesis polymerization in the presence of the ruthenium complex compound of the present invention. In the process of the present invention for producing a ring-opened cyclic olefin polymer, dicyclopentadiene is preferably used as the cyclic olefin.

Sixth, the present invention provides a process for producing a hydrogenated product of ring-opened cyclic olefin polymer, comprising a step of polymerizing a cyclic olefin by ring-opening metathesis polymerization in the presence of the ruthenium complex compound of the present invention and a step of hydrogenating carbon-carbon double bonds in the obtained polymer. In the process of the present invention for producing a hydrogenated product of ring-opened cyclic olefin polymer, dicyclopentadiene is preferably used as the cyclic olefin.

Seventh, the present invention provides a hydrogenated product of ring-opened dicyclopentadiene polymer having a weight-average molecular weight of 1,000–500,000 determined by gel permeation chromatography and expressed in terms of polystyrene, an iodine value of 20 or less, and a glass transition temperature measured by a differential scanning calorimeter of 100° C. or more.

The hydrogenated product of ring-opened dicyclopentadiene polymer of the present invention is preferably a polymer obtained by the process of the present invention for producing a hydrogenated ring-opened cyclic olefin polymer.

BEST MODE FOR CARRYING OUT THE INVENTION

Figure 1:
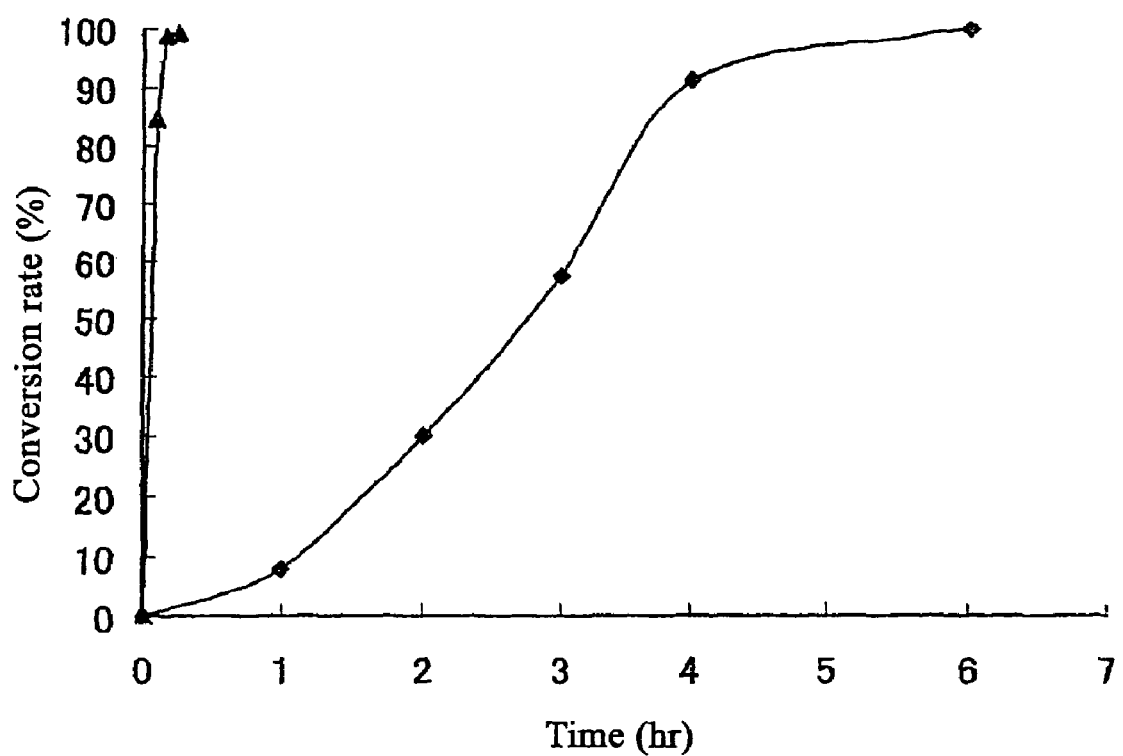
FIG. 1 shows the change in the polymerization conversion rate over the reaction time in Example 6 and Comparative Example 2.

The present invention will be described in detail in the following sections: (1) Ruthenium complex compound, (2) Process for producing ruthenium complex compound, (3) Metathesis reaction catalyst, (4) Hydrogenation catalyst, (5) Process for producing ring-opened cyclic olefin polymer, (6) Process for producing hydrogenated ring-opened cyclic olefin polymer, and (7) Hydrogenated dicyclopentadiene ring-opened polymer.

(1) Ruthenium Complex Compound

The first of the present invention provides a novel ruthenium complex compound. The ruthenium complex compound of the present invention comprises a hetero atom-containing carbene compound having at least one six-membered ring structure bonded to ruthenium.

The hetero atom-containing carbene compound having a six-membered ring structure is a compound having at least one hetero atom and at least one methylene free radical in the six-membered ring structure. The methylene free radical is a non-charged divalent carbon atom having a bonding site and is shown by (>C:).

Here, the hetero atom refers to an atom belonging to the group XV or group XVI in the Periodic Table. Specific examples of the hetero atom include N, O, P, S, As, and Se. Of these hetero atoms, N, O, P, S are preferable for obtaining a stable carbene compound. N and P are more preferable, with N being particularly preferable.

As a particularly preferable N-containing carbene compound having a six-membered ring structure, a hexahydropyrimidin-2-ylidene derivative of the following formula [1] can be given.

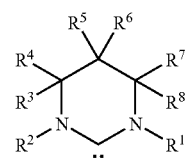

In the formula, $R^1$–$R^8$ independently represent a hydrogen atom, a halogen atom, or a hydrocarbon group. At least two of $R^1$–$R^8$ may be bonded together to form a ring.

Examples of the halogen atom include fluorine, chlorine, and bromine. As the hydrocarbon group, a hydrocarbon group having 1–20 carbon atoms can be given.

Specific examples of the hydrocarbon group having 1–20 carbon atoms include an alkyl group, alkenyl group, alkynyl group, and aryl group. The alkyl group, alkenyl group, or alkynyl group may be linear, branched, or cyclic. One or more hydrogen atoms in the hydrocarbon group may be substituted with a functional group such as a nitro group, nitroso group, alkoxyl group, aryloxy group, amide group, carboxyl group, carbonyl group, silyl group, or sulfonyl group, or with a halogen atom.

Of these hydrocarbon groups, an alkyl group having 1–20 carbon atoms or an aryl group having 6–20 carbon atoms is preferable. Specific examples of such a group include alkyl groups having 1–20 carbon atoms such as methyl group, ethyl group, isopropyl group, sec-butyl group, isobutyl group, t-butyl group, n-butyl group, n-pentyl group, neopentyl group, t-pentyl group, n-hexyl group, and isohexyl group; cycloalkyl groups having 3–8 carbon atoms such as a cyclopentyl group and cyclohexyl group; aralkyl groups having 7–20 carbon atoms such as benzyl group, 1-phenylethyl group, 1-(α-naphthyl)ethyl group, and 1-(β-naphthyl)ethyl group; functional group-containing alkyl groups having 1–20 carbon atoms such as 1-(1,2,2-trimethylpropoxycarbonyl)ethyl group, 2-(1,2,2-trimethylpropoxycarbonyl)ethyl group, 1-(ethoxycarbonyl)ethyl group, and 2-(ethoxycarbonyl)ethyl group; and substituted or unsubstituted aryl groups such as phenyl group, 2-methylphenyl group, 3-methylphenyl group, 4-methylphenyl group, 2,4-dimethylphenyl group, 2,6-diethylphenyl group, 2,6-diisopropylphenyl group, mesityl group, 3,5-dimethoxyphenyl group, 2-aminophenyl group, 4-aminophenyl group, 2-hydroxyphenyl group, 4-hydroxyphenyl group, 2-chlorophenyl group, 4-chlorophenyl group, 2-nitrophenyl group, 4-nitrophenyl group, 2-acetoxyphenyl group, 4-acetoxyphenyl group, α-naphthyl group, and β-naphthyl group.

In the present invention, for some reasons such as ease of synthesis and excellent catalytic activity, the compound of the above formula [1] is preferably a compound in which $R^1$ and $R^2$ are independently an alkyl group having 1–20 carbon atoms or an aryl group having 6–20 carbon atoms, with $R^3$–$R^8$ being still more preferably hydrogen atoms.

The ruthenium complex compound of the present invention, which comprises a hetero atom-containing carbene compound having at least one six-membered ring structure bonded to ruthenium, is preferably a ruthenium complex compound of the following formula [2].

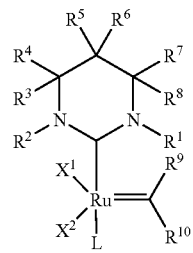

[2]

In the formula, $R^1$–$R^8$ are the same as defined for the formula [1].

$X^1$ and $X^2$ independently represent an anionic ligand and L represents a neutral ligand.

$R^9$ and $R^{10}$ independently represent a hydrogen atom or an organic group.

As Examples of the organic group, an alkyl group having 1–20 carbon atoms, alkenyl group having 2–20 carbon atoms, alkynyl group having 2–20 carbon atoms, aryl group having 6–20 carbon atoms, carboxylate group having 1–20 carbon atoms, alkoxyl group having 1–20 carbon atoms, alkenyloxy group having 2–20 carbon atoms, alkynyloxy group having 2–20 carbon atoms, aryloxy group having 6–20 carbon atoms, alkoxycarbonyl group having 2–20 carbon atoms, alkylthio group having 1–20 carbon atoms, arylthio group having 6–20 carbon atoms, alkylsulfonyl group having 1–20 carbon atoms, alkynylsulfinyl group having 1–20 carbon atoms, and the like can be given. The organic group may be substituted with a group containing an atom selected from the group consisting of an oxygen atom, nitrogen atom, sulfur atom, phosphorus atom, and silicon atom, or with a halogen atom. In the ruthenium complex compound of the formula [2], it is preferable that either $R^9$ or $R^{10}$ be a hydrogen atom and the other be the above organic group. It is still more preferable that either $R^9$ or $R^{10}$ be a hydrogen atom and the other be an alkoxyl group having 1–20 carbon atoms or an aryl group having 6–20 carbon atoms.

As the anionic ligands ($X^1$ and $X^2$), any ligands having negative charges when separated from the central metal (Ru) may be used.

Specific examples of the anionic ligands ($X^1$ and $X^2$) include a hydrogen atom; a halogen atom such as fluorine, chlorine, bromine, and iodine; a diketonate group such as an acetylacetonate group; a substituted or unsubstituted cyclopentadienyl group, a substituted or unsubstituted allyl group, an alkenyl group, an alkyl group, an aryl group, an alkoxyl group, an aryloxy group, an alkoxycarbonyl group, a carboxyl group, an alkylsulfonate group, an arylsulfonate group, an alkylthio group, an alkenylthio group, an, arylthio group, an alkylsulfonyl group, and an alkylsulfinyl group. Of these, a halogen atom is preferable.

As the neutral ligand (L), any ligands having neutral charges when separated from the central metal may be used. A hetero atom-containing carbene compound of the above formula [1] having a six-membered ring structure may be used.

Specific examples of the neutral ligand (L) include an oxygen atom, water, carbon monoxide (carbonyl), amines, pyridines, ethers, nitriles, esters, phosphines, phosphinites, phosphites, sulfoxides, thioethers, amides, aromatic compounds, cyclic diolefins, olefins, isocyanides, thiocyanates, and a hetero atom-containing carbene compound of the formula [1] having a six-membered ring structure. Of these, pyridines and phosphines are preferable, with phosphines being particularly preferable. As examples of the phosphines, trimethylphosphine, triethylphosphine, tri-n-propylphosphine, tri-n-butylphosphine, tricyclohexylphosphine, tri(4-methylcyclohexyl)phosphine, triphenylphosphine, tri (2,4,6-trimethylphenyl)phosphine, and the like can be given.

Specific examples of the ruthenium complex compound of the formula (2) include (1,3-diisopropyltetrahydropyrimidin-2-ylidene)(benzylidene) (tricyclohexylphosphine)ruthenium dichloride, (1,3-dibenzyltetrahydropyrimidin-2-ylidene)(benzylidene) (tricyclohexylphosphine)ruthenium dichloride,(1,3-diphenyltetrahydropyrimidin-2-ylidene) (benzylidene) (tricyclohexylphosphine)ruthenium dichloride, [1,3-di(4'-methylphenyl)tetrahydropyrimidin-2-ylidene] (benzylidene)(tricyclohexylphosphine)ruthenium dichloride, [1,3-di(2',4'-dimethylphenyl)tetrahydropyrimidin-2-ylidene](benzylidene) (tricyclohexylphosphine)ruthenium dichloride, (1,3-dimesityltetrahydropyrimidin-2-ylidene)(benzylidene) (tricyclohexylphosphine)ruthenium dichloride, (1,3-dicyclohexyltetrahydropyrimidin-2-ylidene)(benzylidene)(tricyclohexylphosphine)ruthenium dichloride, (1,3-diisopropyltetrahydropyrimidin-2-ylidene) (ethoxymethylene)(tricyclohexylphosphine)ruthenium dichloride, (1,3-diphenyltetrahydropyrimidin-2-ylidene)(ethoxymethylene)(tricyclohexylphosphine)ruthenium dichloride, [1,3-di(4'-methylphenyl)tetrahydropyrimidin-2-ylidene] (ethoxymethylene)(tricyclohexylphosphine)ruthenium dichloride, [1,3-di(2',4'-dimethylphenyl)tetrahydropyrimidin-2-ylidene] (ethoxymethylene)(tricyclohexylphosphine)ruthenium dichloride, (1,3-dimesityltetrahydropyrimidin-2-ylidene) (ethoxymethylene)(tricyclohexylphosphine)ruthenium dichloride, [1,3-di(2'-propenyl)tetrahydropyrimidin-2-ylidene] (ethoxymethylene)(tricyclohexylphosphine)ruthenium dichloride, [1,3-di(1'-phenylethyl)isopropyltetrahydropyrimidin-2-ylidene] (ethoxymethylene)(tricyclohexylphosphine)ruthenium dichloride, and (1,3-dicyclohexyltetrahydropyrimidin-2-ylidene) (ethoxymethylene)(tricyclohexylphosphine)ruthenium dichloride.

(2) Process for Producing Ruthenium Complex Compound

The second of the present invention provides a process for producing the ruthenium complex compound of the present invention. The ruthenium complex compound of the present invention can be produced by reacting a ruthenium complex compound having a neutral ligand with the above hetero atom-containing carbene compound having a six-membered ring structure (ligand exchange reaction).

As the neutral ligand, any ligands having neutral charges may be used without specific limitations. As specific examples of the neutral ligand, the same compounds listed for the neutral ligand (L) can be given.

A carbene compound of the above formula [1] can be synthesized by a conventional method such as the method described in Chemical Communications., pp. 241–242, 1999. The method described in WO 00/15339 for producing a heterocyclic carbene compound having a five-membered ring structure may also be used for synthesis.

As a specific example of the method for synthesizing a carbene compound of the formula [1], a method comprising adding a base to a solution of a 1,3-disubstituted-1,4,5,6-tetrahydropyrimidinium salt in an aprotic solvent and stirring the mixture can be given.

As examples of a 1,3-disubstituted-1,4,5,6-tetrahydropyridinium salt used, tetrafluoroborate, hexafluorophosphate, perchlorate, and the like can be given. Examples of the base used include metal hydrides such as sodium hydride, lithium hydride, and potassium hydride; lithium amides such as lithium diisopropylamide and lithium bis(trimethylsilyl) amide; organolithiums such as n-butyl lithium, sec-butyl lithium, and t-butyl lithium; and metal alkoxides such as sodium methoxide, sodium ethoxide, potassium methoxide, potassium ethoxide, and potassium t-butoxide. These bases may be used either alone or in combination of two or more. Examples of the aprotic solvent used include ethers such as diethyl ether, diisopropyl ether, tetrahydrofuran, and 1,2-dimethoxyethane; and amides such as N,N-dimethylformamide, N,N-dimethylacetamide, and hexamethylphosphoramide. A mixed solvent obtained by adding ammonia to the aprotic solvent may also be used.

The reaction can be carried out in the temperature range from −100° C. to the boiling point of the using solvent.

The hetero atom-containing carbene compound having a six-membered ring structure obtained by the above reaction can be used for ligand exchange reaction as is without any separation or purification. Since the hetero atom-containing carbene compound having a six-membered ring structure used in the present invention is stable and can be separated, a separated or purified product of the carbene compound can also be used for ligand exchange reaction.

Ligand exchange reaction can be carried out in an inert solvent. The solvent used is not specifically limited, insofar as the solvent is inert. Examples of the solvent that can be used include an ether solvent, ketone solvent, ester solvent, halogenated hydrocarbon, aromatic hydrocarbon, and aliphatic hydrocarbon. Of these, an ether or aromatic hydrocarbon is particularly preferably used, since the target ruthenium complex compound can be obtained at a high yield. Examples of the ether include diethyl ether, diisopropyl ether, tetrahydrofuran, and 1,2-dimethoxyethane. Examples of the aromatic hydrocarbon include benzene, toluene, and xylene.

The amount of the hetero atom-containing carbene compound having a six-membered ring structure used in ligand exchange reaction is not specifically limited, insofar as the amount is one mol or more for one mol of the ruthenium complex compound having a neutral ligand (raw material). The ligand exchange reaction usually proceeds quantitatively. Therefore, when the hetero atom-containing carbene compound is used in an amount almost equimolar with the raw material, a hetero atom-containing carbene compound having one six-membered ring structure can be obtained. When the amount of the hetero atom-containing carbene compound used is twice or more the amount of the raw material (in molar equivalent), a ruthenium complex compound with a hetero atom-containing carbene compound having one or two six-membered ring structures being bonded to ruthenium can be obtained.

The reaction temperature is not specifically limited, insofar as the target ruthenium complex compound can be present in a stable manner. The temperature is in the range of usually −100° C. to +200° C., preferably −80° C. to +150° C., and still more preferably −40° C. to +100° C. The reaction time is preferably from one minute to 24 hours, and still more preferably from 10 minutes to five hours.

In the process for producing the ruthenium complex compound of the present invention, all operations are preferably carried out in an atmosphere of inert gas such as nitrogen gas, argon gas, or helium gas.

(3) Metathesis Reaction Catalyst

The third of the present invention provides a metathesis reaction catalyst for an olefin compound, comprising the ruthenium complex compound of the present invention. The metathesis reaction catalyst of the present invention comprises one or more types of the ruthenium complex compound of the present invention.

Metathesis reaction of an olefin compound includes any reactions conventionally referred to as olefin metathesis reaction (see K. J. Ivin and J. C. Mol, Olefin Metathesis and Metathesis Polymerization, Academic Press, Tokyo, and so on). As examples of such metathesis reaction, ring-opening metathesis polymerization, ring-closing metathesis reaction, cross metathesis reaction of an acyclic olefin, and metathesis polymerization of an acyclic diene.

The type of the olefin compound used is not specifically limited, insofar as the compound has at least one carbon-carbon double bond in the molecule.

The metathesis reaction catalyst of the present invention is also useful for a metathesis reaction catalyst for an olefin compound having a functional group.

As a functional group in the olefin compound, a functional group containing a halogen atom, oxygen atom, nitrogen atom, sulfur atom, phosphorus atom, silicon atom, or the like can be given. Specific examples of the functional group include an alkoxyl group, carboxyl group, alkenyloxy group, alkynyloxy group, aryloxy group, alkoxycarbonyl group, alkylthio group, arylthio group, alkylamino group, arylamino group, alkylamide group, arylamide group, alkylsilyl group, arylsilyl group, alkylsulfonyl group, alkylsulfinyl group, nitro group, nitroso group, and cyano group.

Metathesis reaction can be carried out in the presence or absence of a solvent. The solvent can be appropriately selected according to the type of the olefin compound used in the reaction. Not only a nonpolar solvent but also a polar solvent may be used, since the ruthenium complex compound of the present invention is stable not only in a nonpolar solvent but also in a polar solvent.

As examples of the nonpolar solvent, linear aliphatic hydrocarbons such as n-pentane, n-hexane, and n-heptane; alicyclic hydrocarbons such as cyclopentane, cyclohexane, methylcyclohexane, dimethylcyclohexane, trimethylcyclohexane, ethylcyclohexane, diethylcyclohexane, decahydronaphthalene, bicycloheptane, tricyclodecane, and cyclooctane; and aromatic hydrocarbons such as benzene, toluene, xylene, tetrahydronaphthalene, and the like can be given.

As examples of the polar solvent, nitro compounds such as nitromethane and nitrobenzene; nitrile compounds such as acetonitrile and benzonitrile; ethers such as diethyl ether and tetrahydrofuran; alcohols such as methanol, ethanol, n-propyl alcohol, isopropyl alcohol, n-butyl alcohol, and t-butyl alcohol; halogenated hydrocarbons such as dichloromethane, chloroform, carbon tetrachloride, and 1,2-dichloroethane; water, and the like can be given. These solvents can be used either alone or in combination of two or more. Of these, common industrial solvents such as linear aliphatic hydrocarbons, alicyclic hydrocarbons, aromatic hydrocarbons, ethers, alcohols, halogenated hydrocarbons, and water are preferably used.

Although the mixing ratio of the olefin compound and the solvent is not specifically limited, the concentration of the olefin compound in the reaction solution is usually 1–100 wt %, preferably 2–100 wt %, and still more preferably 5–100 wt % in metathesis reaction. If the concentration of the olefin compound is less than 1 wt %, productivity of the polymer decreases.

Although the amount of the ruthenium complex compound used for the olefin compound is not specifically limited, the molar ratio of (metal ruthenium in the catalyst):(olefin compound) is in the range of usually 1:100–1:2,000,000, preferably 1:500–1:1,000,000, and still more preferably 1:1,000–1:500,000. If the amount of the catalyst used is too large, it is difficult to remove the catalyst. If the amount of the catalyst is too small, sufficient reactivity cannot be obtained.

The reaction temperature for metathesis reaction may be appropriately set according to the type of the metathesis reaction and the type of the olefin compound to be reacted. The temperature is usually from −80° C. to +200° C. If the reaction temperature is too low, the reaction rate is reduced. If the reaction temperature is too high, the ruthenium complex compound may be decomposed. The reaction time, which may be appropriately set according to the type of the reaction, is usually from one minute to one week.

(4) Hydrogenation Catalyst

The fourth of the present invention provides a hydrogenation catalyst for an olefin compound, comprising the ruthenium complex compound of the present invention. The hydrogenation catalyst of the present invention comprises one or more types of the ruthenium complex compound of the present invention.

The olefin compound used for hydrogenation is not specifically limited, insofar as the compound has at least one carbon-carbon double bond in the molecule, and may be appropriately selected according to the intended application.

Hydrogenation can be carried out by causing an olefin compound to come in contact with hydrogen using or without using a solvent in the presence of the ruthenium complex compound of the present invention. The solvent may be appropriately selected according to the type of the olefin compound to be hydrogenated. Not only a nonpolar solvent but also a polar solvent such as water or an alcohol may be used. Specific examples of the solvent used are the same listed solvents that can be used for metathesis reaction.

Although the amount of the ruthenium complex compound used for hydrogenation is not specifically limited, the molar ratio of (metal ruthenium in the catalyst):(olefin compound) is in the range of usually 1:100–1:2,000,000, preferably 1:500–1:1,000,000, and still more preferably 1:1,000–1:500,000. The pressure of hydrogen used for hydrogenation is usually 10 MPa or less, preferably 0.01–8 MPa, and still more preferably 0.05–5 MPa. The reaction temperature and the reaction time for hydrogenation may also be appropriately set in the same ranges as defined for the metathesis reaction of an olefin compound described above.

After polymerizing an olefin compound by ring-opening metathesis polymerization using the ruthenium complex compound of the present invention, the produced polymer may be successively hydrogenated without separation. In this case, the ruthenium complex compound used as the catalyst for ring-opening metathesis polymerization may also be used as the hydrogenation catalyst as is.

(5) Process for Producing Ring-opened Cyclic Olefin Polymer

The fifth of the present invention provides a process for producing a ring-opened cyclic olefin polymer, comprising polymerizing a cyclic olefin by ring-opening metathesis polymerization in the presence of the ruthenium complex compound of the present invention. The ruthenium complex compound of the present invention is a highly active catalyst for, in particular, ring-opening metathesis reaction of a cyclic olefin compound.

The ring-opened polymer of a cyclic olefin can be obtained by polymerizing a cyclic olefin by ring-opening metathesis polymerization using the ruthenium complex compound of the present invention as a metathesis reaction catalyst.

As the cyclic olefin used in the present invention, a monocyclic olefin monomer, a norbornene monomer such as norbornenes, dicyclopentadienes, or tetracyclododecenes, or the like can be given. The cyclic olefin may be substituted with a hydrocarbon group such as an alkyl group, an alkenyl group, an alkylidene group, or an aryl group, or a polar group such as an alkoxycarbonyl group or carboxyl group. In addition to the double bond in the norbornene ring, the norbornene monomer may have a further double bond.

As the monocyclic olefin, a cyclic monoolefin or cyclic diolefin having usually 4–20, and preferably 4–10, carbon atoms can be given. As specific examples of the cyclic monoolefin, cyclobutene, cyclopentene, methylcyclopentene, cyclohexene, methylcyclohexene, cycloheptene, cyclooctene, and the like can be given. Specific examples of the cyclic diolefin include cyclohexadiene, methylcyclohexadiene, cyclooctadiene, methylcyclooctadiene, and phenylcyclooctadiene.

Specific examples of the norbornene monomer include dicyclopentadienes such as dicyclopentadiene, methyl-dicyclopentadiene, and dihydrodicyclopentadiene (tricyclo[4.3.1$^{2,5}$.0]deca-3-ene); tetracyclododecenes such as tetracyclododecene, 8-methyltetracyclododecene, 8-ethyltetracyclododecene, 8-cyclohexyltetraclododecene, 8-cyclopentyltetracyclododecene, 8-methylidenetetracyclododecene, 8-ethylidenetetracyclododecene, 8-vinyltetracyclododecene, 8-propenyltetracyclododecene, 8-cyclohexenyltetracyclododecene, 8-cyclopentenyltetracyclododecene, 8-phenyltetracyclododecene, 8-methoxycarbonyltetracyclododecene, 8-methyl-8-methoxycarbonyltetracyclododecene, 8-hydroxymethyltetracyclododecene, 8-carboxytetraclododecene, tetracyclododecene-8,9-dicarboxylic acid, tetracyclododecene-8,9-dicarboxylic anhydride, 8-cyanotetracyclododecene, tetracyclododecene-8,9-dicarboximide, 8-chlorotetracyclododecene, and 8-trimethoxysilyltetracyclododecene; norbornenes such as norbornene, 5-methylnorbornene, 5-ethylnorbornene, 5-butylnorbornene, 5-hexylnorbornene, 5-decylnorbornene, 5-cyclohexylnorbornene, 5-cyclopentylnorbornene, 5-ethylidenenorbornene, 5-vinylnorbornene, 5-propenylnorbornene, 5-cyclohexenylnorbornene, 5-cyclopentenylnorbornene, 5-phenylnorbornene, tetracyclo[6.5.1$^{2,5}$.0$^{1,6}$.0$^{8,13}$]trideca-3,8,10,12-tetraene (also-called 1,4-methano-1,4,4a,9a-tetrahydrofluorene), tetracyclo[6.6.1$^{2,5}$.0$^{1,6}$.0$^{8,13}$]tetradeca-3,8,10,12-tetraene (also called 1,4-methano-1,4,4a,5,10,10a-hexahydroanthracene), 5-methoxycarbonylnorbornene, 5-ethoxycarbonylnorbornene, 5-methyl-5-methoxycarbonylnorbornene, 5-methyl-5-ethoxycarbonylnorbornene, norbornenyl-2-methyl. propionate, norbornenyl-2-methyl octanoate, norbornene-5,6-dicarboxylic anhydride, 5-hydroxymethylnorbornene, 5,6-di(hydroxymethyl)norbornene, 5,5-di(hydroxymethyl)norbornene, 5-hydroxy-isopropylnorbornene, 5,6-dicarboxynorbornene, and 5-methoxycarbonyl-6-carboxynorbornene; oxanorbornenes such as oxanorbornene, 5-methyloxanorbornene, 5-ethyloxanorbornene, 5-butyloxanorbornene, 5-hexyloxanorbornene, 5-decyloxanorbornene, 5-cyclohexyloxanorbornene, 5-cyclopentyloxanorbornene, 5-phenyloxanorbornene, 5-ethylideneoxanorbornene, 5-vinyloxanorbornene, 5-propenyloxanorbornene, 5-cyclohexenyloxanorbornene, 5-cyclopentenyloxanorbornene, 5-methoxycarbonyloxanorbornene, 5-ethoxycarbonyloxanorbornene, 5-methyl-5-methoxycarbonyloxanorbornene, 5-methyl-5-ethoxycarbonyloxanorbornene, oxanorbornenyl-2-methyl propionate, oxanorbornenyl-2-methyl octanoate, oxanorbornene-5,6-dicarboxylic anhydride, 5-hydroxymethyloxanorbornene, 5,6-di(hydroxymethyl)oxanorbornene, 5,5-di(hydroxymethyl)oxanorbornene, 5-hydroxy-isopropyloxanorbornene, 5,6-dicarboxyoxanorbornene, 5-methoxycarbonyl-6-carboxyoxanorbornene, 5-cyanooxanorbornene, and oxanorbornene-5,6-dicarboximide; and hexacycloheptadecenes such as hexacycloheptadecene, 12-methylhexacycloheptadecene, 12-ethylhexacycloheptadecene, 12-butylhexacycloheptadecene, 12-hexylhexacycloheptadecene, 12-decylhexacycloheptadecene, 12-cyclohexylhexacycloheptadecene, 12-cyclopentylhexacycloheptadecene, 12-ethylidenehexacycloheptadecene, 12-vinylhexacycloheptadecene, 12-propenylhexacycloheptadecene, 12-cyclohexenylhexacycloheptadecene, and 12-cyclopentenylhexacycloheptadecene.

These cyclic olefins may be used either alone or in combination of two or more. Of these, norbornene monomers are preferably used, with dicyclopentadiene being particularly preferably used.

A cyclic olefin may be polymerized by ring-opening metathesis polymerization (hereinafter may be referred to as "polymerization") in the presence or absence of a solvent. The solvent used is not specifically limited, insofar as the produced polymer can be dissolved in the solvent under specific conditions and the solvent does not affect polymerization.

As specific examples of the solvent, linear aliphatic hydrocarbons such as n-pentane, n-hexane, and n-heptane; alicyclic hydrocarbons such as cyclopentane, cyclohexane, methylcyclohexane, dimethylcyclohexane, trimethylcyclohexane, ethylcyclohexane, diethylcyclohexane, decahydronaphthalene, bicycloheptane, tricyclodecane, and cyclooctane; aromatic hydrocarbons such as benzene, toluene, xylene, and tetrahydronaphthalene; nitro compounds such as nitromethane and nitrobenzene; nitrile compounds such as acetonitrile and benzonitrile; and ether compounds such as diethyl ether and tetrahydrofuran; and the like can be given.

Of these, common industrial solvents such as linear aliphatic hydrocarbons, alicyclic hydrocarbons, and aromatic hydrocarbons are preferably used. In view of excellent solubility of the polymer and the like, alicyclic hydrocarbon solvents such as cyclohexane are still more preferably used.

Although the mixing ratio of the cyclic olefin (monomer) and the solvent is not specifically limited, the concentration of the cyclic olefin in the reaction solution is usually 1–50 wt %, preferably 2–45 wt %, and still more preferably 5–40 wt %. If the concentration of the cyclic olefin is less than 1 wt %, productivity of the polymer decreases. If the concentration is more than 50 wt %, solution viscosity during polymerization is too high, whereby it is difficult to stir the reaction solution.

In ring-opening metathesis polymerization, although the amount of the ruthenium complex compound (catalyst) used for the cyclic olefin (monomer) is not specifically limited, the molar ratio of (metal ruthenium in the catalyst):(cyclic olefin) is usually 1:100–1:2,000,000, preferably 1:500–1:1,000,000, and still more preferably 1:1,000–1:500,000. If the amount of the catalyst used is too large, it is difficult to remove the catalyst. If the amount is too small, sufficient polymerization activity cannot be obtained.

Polymerization is initiated by mixing the reaction solution containing the monomer and the solvent described above with the ruthenium complex compound. Although the polymerization temperature is not specifically limited, the temperature is usually from −30° C. to +200° C., and preferably from 0° C. to 180° C. The polymerization time is usually from one minute to 100 hours.

During polymerization, a molecular weight modifier for a polymer may be added to the reaction system. As an example of the molecular weight modifier, a compound having a vinyl group can be given. Specific examples of such a compound include α-olefins such as 1-butene, 1-pentene, 1-hexene, and 1-octene; styrenes such as styrene and vinyltoluene; ethers such as ethyl vinyl ether, isobutyl vinyl ether, and allyl glycidyl ether; halogen-containing vinyl compounds such as allyl chloride; vinyl ester compounds such as allyl acetate, allyl alcohol, and glycidyl methacrylate; and nitrogen-containing vinyl compounds such as acrylamide. The amount of the vinyl compound used may be appropriately set according to the molecular weight of the target polymer. The amount is usually 0.1–10 mol % for the cyclic olefin.

Polymerization can be terminated by optionally adding the above vinyl compound again and releasing the ruthenium complex compound from the growth terminal of the polymer. This polymerization termination method is useful for improving activity of the catalyst used in the hydrogenation step when the polymer is hydrogenated successively after polymerization.

(6) Process for Producing Hydrogenated Product of Ring-opened Cyclic Olefin Polymer The sixth of the present invention provides a process for producing a hydrogenated product of ring-opened cyclic olefin polymer, comprising a step of polymerizing a cyclic olefin by ring-opening metathesis polymerization in the presence of the ruthenium complex compound of the present invention and a step of hydrogenating carbon-carbon double bonds in the obtained polymer.

The ruthenium complex compound of the present invention exhibits high activity as a hydrogenation catalyst for selectively hydrogenating carbon-carbon double bonds in an olefin compound. Therefore, in the present invention, the ruthenium complex compound used as the catalyst during ring-opening metathesis polymerization can be used as the hydrogenation catalyst as is. Hydrogenation may also be carried out by further adding the ruthenium complex compound after the step of polymerizing a cyclic olefin by ring-opening metathesis polymerization.

Alternatively, a hydrogenated product of ring-opened cyclic olefin polymer may be obtained by hydrogenating a ring-opened polymer of a cyclic olefin obtained by employing the ruthenium complex compound of the present invention, using a hydrogenation catalyst containing at least one type of metal selected from nickel, cobalt, iron, titanium, rhodium, palladium, platinum, ruthenium, rhenium, and the like.

These hydrogenation catalysts (the ruthenium complex compound of the present invention and the hydrogenation catalyst containing at least one type of metal selected from nickel, cobalt, iron, titanium, rhodium, palladium, platinum, ruthenium, rhenium, and the like) may be used alone or in combination of two or more.

The amount of the hydrogenation catalyst used is usually 0.01–50 parts by weight, preferably 0.05–20 parts by weight, and still more preferably 0.1–10 parts by weight for 100 parts by weight of the polymer. The hydrogenation temperature is usually 10–250° C., preferably 50–200° C., and still more preferably 80–180° C. The pressure of hydrogen is usually 0.1–30 MPa, preferably 1–20 MPa, and still more preferably 2–10 MPa. The hydrogenation time is usually 0.5–50 hours.

The hydrogenated product can be isolated by using a method known in the art such as a method of precipitating the product from the reaction solution by adding a poor solvent such as a lower aliphatic alcohol, a method of evaporating the solvent, or a method of introducing steam into the reaction solution (steam stripping).

In the manner as above, 50% or more, preferably 80% or more, and still more preferably 90% or more of carbon-carbon double bonds in the ring-opened polymer are hydrogenated, whereby a hydrogenated product of ring-opened cyclic olefin polymer can be obtained.

A solvent is preferably used in hydrogenation. Specific examples of the solvent are the same listed solvents that can be used for polymerizing a cyclic olefin by ring-opening metathesis polymerization.

The production process of the present invention can be suitably used for production of a hydrogenated product of ring-opened metathesis polymer of norbornene monomers among cyclic olefins.

When a norbornene monomer is subjected to ring-opening metathesis polymerization using the ruthenium complex compound comprising a hetero atom-containing carbene compound having a six-membered ring structure bonded to ruthenium, a polymer having a stereostructure differing from that of a polymer synthesized using a conventional catalyst can be obtained. The present invention provides a novel hydrogenated ring-opened polymer having physical properties differing from those of a conventional hydrogenated ring-opened polymer.

The production process of the present invention can be particularly preferably used for hydrogenating a polymer obtained by polymerizing dicyclopentadiene (DCP) among norbornene monomers by ring-opening metathesis polymerization. A hydrogenated product of ring-opened dicyclopentadiene (DCP) polymer having a Tg significantly higher than the Tg of a conventional hydrogenated product of ring-opened DCP polymer can be produced by hydrogenating a polymer obtained by polymerizing DCP by ring-opening metathesis polymerization using the ruthenium complex compound of the present invention.

(7) Hydrogenated Product of Ring-opened Dicyclopentadiene Polymer

The seventh of the present invention provides a hydrogenated product of ring-opened dicyclopentadiene polymer (hereinafter referred to as "hydrogenated ring-opened DCP polymer") having specific physical properties. The hydrogenated ring-opend DCP polymer of the present invention is preferably a polymer obtained by the process of the present invention for producing a hydrogenated ring-opened cyclic olefin polymer.

The hydrogenated ring-opened DCP polymer of the present invention is amorphous and has a weight-average molecular weight of 1,000–500,000determined by gel permeation chromatography and expressed in terms of polystyrene. To improve heat resistance, the weight average molecular weight is preferably 2,000 or more, and still more preferably 5,000 or more.

The iodine value of the hydrogenated ring-opened DCP polymer of the present invention is 20 or less, preferably 10 or less, and still more preferably 5 or less. The smaller the iodine value is, the higher the Tg is.

The Tg of the hydrogenated ring-opened DCP polymer of the present invention measured by a differential scanning calorimeter is 100° C. or more, preferably 102° C. or more, and still more preferably 105° C. or more. In view of heat resistance, the hydrogenation degree of a hydrogenated ring-opened cyclic olefin polymer is preferably as high as possible.

The hydrogenated ring-opened DCP polymer of the present invention having excellent properties as described above can be preferably used as a part or formed product for medical appliances or electric components.

EXAMPLES AND COMPARATIVE EXAMPLES

The present invention will now be described in detail by way of examples and comparative examples, which should not be construed as limiting the present invention. In the examples and comparative examples, "part(s)" means "part(s) by weight" and "%" means "wt %" unless otherwise indicated.

(1) The structure of the synthesized ruthenium complex compound was identified by elemental analysis and measurements of the $^1$H-NMR spectrum, $^{13}$C-NMR spectrum, and $^{31}$P-NMR spectrum.

(2) The polymerization conversion ratio in ring-opening metathesis polymerization was determined by a solid content weight measuring method.

(3) The number-average molecular weight (Mn) and weight-average molecular weight (Mw) of the polymer were determined by gel permeation chromatography (GPC) using HLC-8020 manufactured by Tosoh Corp. with tetrahydrofuran as a solvent and expressed in terms of polystyrene. The molecular weight of the hydrogenated product of the ring-opened polymer was determined by gel permeation chromatography (GPC) using HLC-8121 manufactured by Tosoh Corp. with o-dichlorobenzene as a solvent at 135° C. and expressed in terms of polystyrene.

(4) The hydrogenation degree of carbon—carbon double bonds in the polymer was determined by measuring the $^1$H-NMR spectrum.

(5) The reaction products by ring-closing metathesis reaction and cross metathesis reaction of an acyclic olefin were analyzed using gas chromatography-mass spectrometry (GC-MS).

(6) The glass transition temperature (Tg) and the melting point were measured by a differential scanning calorimeter (DSC) at a temperature elevation rate of 10° C./min.

Example 1

Preparation of (1,3-diisopropyltetrahydropyrimidin-2-ylidene)(ethoxymethylene)(tricyclohexylphosphine) ruthenium dichloride A Schlenk tube was charged with 2.8 parts of 1,3-diisopropyl-1,4,5,6-tetrahydropyrimidinium tetrafluoroborate (a product synthesized by the method described in Tetrahedron Letters., Vol. 32, No. 38, pp. 5031–5034, 1991) and 3 parts of sodium hydride. 130 parts of tetrahydrofuran (THF) and 240 parts of ammonia were added to the mixture. The mixture was stirred at reflux temperature of ammonia for three hours. The solvent was removed under reduced pressure to obtain a residue. 200 parts of n-hexane was added to the residue, and the mixture was sufficiently stirred. The solid component was removed by filtration to obtain a filtrate. The filtrate was added to a separately prepared solution of homogeneously mixed 1 part of bis(tricyclohexylphosphine)ethoxymethyleneruthenium dichloride (RuCl$_2$(═CH(OEt))(P(C$_6$H$_{11}$)$_3$)$_2$) and 130 parts of tetrahydrofuran, and the mixture was stirred at room temperature for two hours. The reaction solvent was removed under reduced pressure to obtain a residue. The residue was washed five times with 70 parts of n-hexane, followed by drying the residue under reduced pressure. The obtained powder was recrystallized from n-hexane to obtain 0.3 part of the target compound. All the above operations were carried out in an argon atmosphere.

Data relating to the properties of the obtained ruthenium complex compound (hereinafter referred to as "catalyst A") is given below.

Elemental analysis values (as C$_{31}$H$_{59}$ON$_2$Cl$_2$PRu) Calculated value: C, 54.85; H, 8.76; N, 4.13 (%) Measured value: C, 54.73; H, 8.74; N, 4.09 (%) $^1$H-NMR (CD$_2$Cl$_2$, room temperature) δppm: 14.77 (d, 1H, J=1.1 Hz, CH (OEt)) $^{31}$P-NMR (CD$_2$Cl$_2$, room temperature) δppm: 38.5 (P(C$_6$H$_{11}$)$_3$) $^{13}$C-NMR (CD$_2$Cl$_2$, room temperature) δppm: 207.9 (d, J=82.2 Hz, NCN)

Example 2

Preparation of (1,3-diisopropyltetrahydropyrimidin-2-ylidene)(benzylidene)(tricyclohexylphosphine) ruthenium dichloride A Schlenk tube was charged with 1.3 parts of 1,3-diisopropyl-1,4,5,6-tetrahydropyridinium tetrafluoroborate. Then, 23 parts of THF and 0.53 part of lithium diisopropylamide were added, and the mixture was stirred at room temperature for one hour. The reaction solution was filtered through celite. The filtrate was added to a separately prepared solution of homogeneously mixed 1 part of bis(tricyclohexylphosphine)benzylideneruthenium dichloride (RuCl$_2$(═CHC$_6$H$_5$) (P(C$_6$H$_{11}$)$_3$)$_2$) and 45 parts of toluene, and the mixture was stirred at room temperature for one hour. The solvent was removed from the reaction solution under reduced pressure to obtain a residue. 41 parts of n-pentane was added to the residue, followed by removing the insoluble matter by filtration through celite. The filtrate was concentrated under reduced pressure to obtain a residue. The residue was dried under reduced pressure to obtain a powder. The obtained powder was cooled to −30° C. and washed with n-pentane to obtain 0.3 part of the target compound. All the above operations were carried out in an argon atmosphere.

Data relating to the properties of the obtained ruthenium complex compound (hereinafter referred to as "catalyst B") is given below.

$^1$H-NMR (C$_6$D$_6$, room temperature) δppm: 20.76 (d, 1H, J=3.7 Hz, CHC$_6$H$_5$) $^{31}$P-NMR (C$_6$D$_6$, room temperature) δppm: 35.0 (P(C$_6$H$_{11}$)$_3$) $^{13}$C-NMR (C$_6$D$_6$, room temperature) δppm: 208.9 (d, J=85 Hz, NCN)

Example 3

Preparation of (1,3-dimesityltetrahydropyrimidin-2-ylidene)(benzylidene)(tricyclohexylphosphine)ruthenium dichloride A Schlenk tube was charged with 1 part of 1,3-dimesityl-1,4,5,6-tetrahydropyrimidinium tetrafluoroborate, 1 part of sodium hydride, and 0.1 part of potassium t-butoxide. 30 parts of THF was added to the mixture, followed by stirring the mixture at room temperature for three hours. The solvent was removed under reduced pressure to obtain a residue. The residue was extracted with 40 parts of n-hexane. The extract was then dried under reduced pressure. The extract was cooled to −78° C. and washed with n-pentane to obtain 0.3 part of a white solid. The white solid was mixed with 0.4 part of (pyridine)(tricyclohexylphosphine)benzylideneruthemiumdichloride. 30 parts of THF was added to the mixture, followed by stirring the mixture for two hours. The reaction solvent was removed under reduced pressure to obtain a residue. The residue was washed with n-pentane and then recrystallized from n-hexane to obtain 0.08 part of the target compound. All the above operations were carried out in an argon atmosphere.

The structural formula of the obtained ruthenium complex compound (hereinafter referred to as "catalyst C") is shown below.

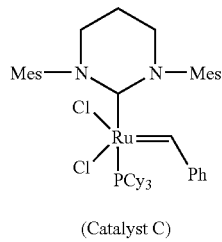

(Catalyst C)

wherein Mes represents a mesityl group and $PCy_3$ represents tricyclohexylphosphine.

Data relating to the properties of the obtained ruthenium complex compound is given below.

$^1$H-NMR (toluene-d8+$CD_2Cl_2$, room temperature) δppm: 19.4 (s, 1H, $CHC_6H_5$) $^{31}$P-NMR (toluene-d8+$CD_2Cl_2$, room temperature) δppm: 27.0 ($P(C_6H_{11})$)

Example 4

Preparation of Hydrogenated DCP Ring-Opened Polymer

An autoclave with a stirrer was charged with 300 parts of cyclohexane and 66.9 parts of dicyclopentadiene. 0.64 part of 1-hexene was added to the mixture as a molecular weight modifier. A solution of 0.02 part of the catalyst A in 9 parts of THF was added to the mixture. The resulting mixture was stirred at 60° C. for one hour, following which 0.3 part of ethyl vinyl ether was added to the mixture to terminate polymerization. A part of the polymerization solution was collected and analyzed to find that the polymerization conversion rate was at least 99%, the Mn was 12,300, and the Mw was 24,900.

Next, hydrogen was supplied to the autoclave to hydrogenate the polymer while stirring the mixture at 150° C. at a hydrogen pressure of 5 MPa for six hours. The resulting hydrogenated DCP ring-opened polymer was found to have a hydrogenation degree of at least 99.9%, an iodine value of 1.2, an Mn of 15,300, and an Mw was 32,300. The Tg was 106° C., and the melting point was not observed.

Comparative Example 1

Preparation of Hydrogenated DCP Ring-Opened Polymer

Polymerization was carried out in the same manner as in Example 4, except for using bis(tricyclohexylphosphine) benzylideneruthenium dichloride (catalyst D) instead of the catalyst A. A part of the polymerization solution was collected and analyzed to find that the yield was 100%, the Mn was 9,800, and the Mw was 19,800.

Next, hydrogen was supplied to the autoclave to hydrogenate the polymer while stirring the mixture at 150° C. at a hydrogen pressure of 5 MPa for six hours. The resulting hydrogenated DCP ring-opened polymer was found to have a hydrogenation degree of at least 99.9%, an iodine value of 3.4, an Mn of 13,200, and an Mw of 27,200. The Tg was 91° C., and the melting point was not observed.

Example 5

Preparation of Hydrogenated DCP Ring-Opened Polymer

An autoclave with a stirrer was charged with 300 parts of cyclohexane and 74.8 parts of dicyclopentadiene. 0.48 part of 1-hexene was added to the mixture as a molecular weight modifier. After the addition of a catalyst solution of 0.016 part of the catalyst B in 9 parts of THF, the mixture was stirred at 60° C. for one hour, following which 0.16 part of ethyl vinyl ether was added to the solution to terminate polymerization. A part of the polymerization solution was collected and analyzed to find that the polymerization conversion rate was at least 99%, the Mn was 23,300, and the Mw was 53,500.

Next, hydrogen was supplied to the autoclave to hydrogenate the polymer while stirring the mixture at 150° C. at a hydrogen pressure of 5 MPa for six hours. The resulting hydrogenated DCP polymer was found to have a hydrogenation degree of at least 99.9%, an iodine value of 2.4, an Mn of 28,900, and an Mw of 67,300. The Tg was 103° C., and the melting point was not observed.

Example 6

Preparation of DCP Ring-Opened Polymer

A Schlenk tube was charged with 31.2 parts of cyclohexane and 1 part of DCP. 0.0063 part of 1-hexene was added to the mixture as a molecular weight modifier. A catalyst solution of the catalyst C (a solution of 1/20,000 part by mol for DCP (0.00033 part) of the catalyst C in 0.65 part of toluene) was added to the mixture. The mixture was stirred at 17° C. while measuring the change in the polymer yield (conversion rate) over the reaction time. The measurement results are shown in Table 1. A chart prepared based on Table 1 is shown in FIG. 1. In FIG. 1, the conversion rate (%) is indicated along the vertical axis, and the reaction time (hr) is indicated along the horizontal axis. In the figure, solid triangles (▲) are values found in this Example.

Comparative Example 2

Preparation of DCP Ring-Opened Polymer

The same experiment as in Example 6 was carried out, except for using 0.00032 part of (1,3-dimesitylimidazolidin-2-ylidene)(benzylidene)(tricyclohexylphosphine)ruthenium dichloride (catalyst E) shown below instead of 0.00033 part of the catalyst C. The mixture of the same components as in Example 6 was stirred at 17° C., while measuring the change in the polymer yield (conversion rate) over the reaction time.

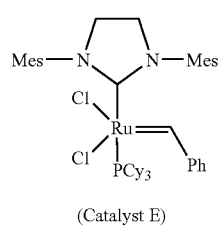

(Catalyst E)

wherein Mes represents a mesityl group and $PCy_3$ represents tricyclohexylphosphine.

The results are shown in Table 1. A chart prepared based on Table 1 is shown in FIG. 1. In FIG. 1, the conversion rate (%) is indicated along the vertical axis and the reaction time (hr) is indicated along the horizontal axis. In the figure, solid squares (■) are values found in this Comparative Example.

TABLE 1

| Reaction time (hr) | Conversion rate (%) | |
|---|---|---|
|  | Example 6 | Comparative Example 2 |
| 0 | 0 | 0 |
| 0.083 | 84.4 | — |
| 0.167 | 98.8 | — |
| 0.25 | 99.2 | — |
| 1 | — | 7.8 |
| 2 | — | 29.8 |
| 3 | — | 57.4 |
| 4 | — | 91.1 |
| 6 | — | 100 |

As is clear from Table 1 and FIG. 1, the ruthenium complex compound of the present invention (catalyst C) exhibited higher catalytic activity than that of the ruthenium complex compound of the Comparative Example (catalyst E).

Example 7

Preparation of Hydrogenated DCP Ring-Opened Polymer

An autoclave with a stirrer was charged with 300 parts of cyclohexane and 74.8 parts of dicyclopentadiene. 0.05 part of 1-hexene was added to the mixture as a molecular weight modifier. A catalyst solution of 0.016 part of the catalyst C in 1 part of toluene was added, and the mixture was stirred at 60° C. for one hour. Then, polymerization was terminated with the addition of 0.16 part of ethyl vinyl ether. A part of the polymerization solution was collected and analyzed to find that the polymerization conversion rate was at least 99%, the Mn was 67,000, and the Mw was 100,500.

Next, hydrogen was supplied to the autoclave to hydrogenate the polymer while stirring the mixture at 150° C. at a hydrogen pressure of 5 MPa for six hours. The resulting hydrogenated DCP ring-opened polymer was found to have a hydrogenation degree of 99.9%, an iodine value of 0.9, an Mn of 70,300, an Mw of 120,100, and a Tg of 107° C. The melting point was not observed.

Example 8

Ring-Closing Metathesis Reaction of 1,7-octadiene

A glass container was charged with a solution of 0.05 part of the catalyst A in 2 parts of 1,2-dichloroethane. After the addition of 0.5 part of 1,7-octadiene, the mixture was reacted at 45° C. for three hours. The reaction mixture was analyzed by GC-MS to find that cyclohexene was obtained at a conversion degree of 98% or more by ring-closing metathesis reaction of 1,7-octadiene.

Example 9

Cross Metathesis Reaction of 1-octene

Reaction was carried out in the same manner as in Example 8, except for using 3.36 parts of 1-octene instead of 0.5 part of 1,7-octadiene. An analysis by GC-MS confirmed that 7-tetradecene was obtained at a conversion degree of 65% by cross metathesis reaction of 1-octene.

Example 10

Preparation of Hydrogenated DCP Ring-Opened Polymer

A polymerization solution containing a DCP ring-opened polymer was obtained in the same manner as in Example 4. 100 parts of the polymerization solution was fed into an autoclave, and 2.0 parts of a nickel catalyst carried on diatom earth was added to the solution as a hydrogenation catalyst. Hydrogenation was carried out by stirring the mixture at 160° C. at a hydrogen pressure of 5 MPa for six hours. The resulting hydrogenated DCP ring-opened polymer was found to have a hydrogenation degree of at least 99.9%, an iodine value of 1.2, an Mn of 15,100, and an Mw of 32,400. The Tg was 106° C., and the melting point was not observed.

INDUSTRIAL APPLICABILITY

The present invention provides a novel ruthenium complex compound comprising a hetero atom-containing carbene compound having a six-membered ring structure bonded to ruthenium. The ruthenium complex compound of the present invention exhibits excellent catalytic activity to metathesis reaction and hydrogenation of an olefin compound and is useful as an active component in a metathesis reaction catalyst and a hydrogenation catalyst.

In the present invention, the ruthenium complex compound of the present invention can be easily and efficiently produced.

In the present invention, a novel hydrogenated ring-opened polymer having physical properties differing from those of a conventional hydrogenated ring-opened polymer can be obtained by polymerizing a cyclic olefin compound by ring-opening metathesis polymerization using the novel ruthenium complex compound, followed by hydrogenating the obtained polymer. When a norbornene monomer is used as the cyclic olefin, a hydrogenated product of ring-opened polymer having a structure differing from that of a polymer synthesized using a conventional catalyst can be produced. The hydrogenated product of ring-opened dicyclopentadiene polymer obtained in the present invention, having excellent properties, in particular, excellent heat resistance, can be preferably used as a part or formed product for medical appliances or electric components.

What is claimed is:

1. A ruthenium complex compound comprising a hetero atom-containing carbene compound having a six-membered ring structure bonded to ruthenium, the carbene compound including at least one hetero atom and at least one methylene free radical in the six-membered ring structure.

2. The compound according to claim 1, shown by the formula:

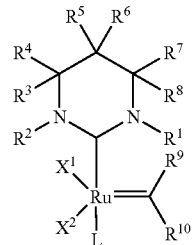

wherein $R^1$–$R^8$ independently represent a hydrogen atom, a halogen atom, or a hydrocarbon group, and at least two of $R^1$–$R^8$ may be bonded together to form a ring, $X^1$ and $X^2$ independently represent an anionic ligand, L represents a neutral ligand, and $R^9$ and $R^{10}$ independently represent a hydrogen atom or an organic group.

3. The compound according to claim 2, wherein $R^1$ and $R^2$ are independently an alkyl group having 1–20 carbon atoms or an aryl group having 6–20 carbon atoms, and either $R^9$ or $R^{10}$ is a hydrogen atom and the other is an alkoxyl group having 1–20 carbon atoms or an aryl group having 6–20 carbon atoms.

4. A process for producing the compound as claimed in claim 1, comprising reacting a ruthenium complex compound having a neutral ligand with a hetero atom-containing carbene compound having a six-membered ring structure.

5. A metathesis reaction catalyst for an olefin compound, comprising the ruthenium complex compound as claimed in claim 1.

6. The metathesis reaction catalyst according to claim 5 for ring-opening metathesis polymerization.

7. A hydrogenation catalyst for an olefin compound, comprising the ruthenium complex compound as claimed in claim 1.

8. A process for producing a ring-opened cyclic olefin polymer, comprising polymerizing a cyclic olefin by ring-opening metathesis polymerization in the presence of the ruthenium complex compound as claimed in claim 1.

9. The process for producing a ring-opened cyclic olefin polymer according to claim 8, wherein dicyclopentadiene is used as the cyclic olefin.

10. A process for producing a hydrogenated product of ring-opened cyclic olefin polymer, comprising a step of polymerizing a cyclic olefin by ring-opening metathesis polymerization in the presence of the ruthenium complex compound as claimed in claim 1, and a step of hydrogenating carbon-carbon double bonds in the obtained polymer.

11. The process for producing a hydrogenated product of ring-opened cyclic olefin polymer according to claim 10, wherein dicyclopentadiene is used as the cyclic olefin.

* * * * *